United States Patent [19]

Tsurumaru et al.

[11] 4,332,646
[45] Jun. 1, 1982

[54] METHOD FOR ASSAYING IRON-EXPOSED PORTION OF COATED STEEL PLATE OR PROCESSED PRODUCT THEREOF

[75] Inventors: Michiko Tsurumaru, Tokyo; Yukio Suzuki; Atsushi Nunokawa, both of Kawasaki, all of Japan

[73] Assignee: Toyo Seikan Kaisha, Ltd., Tokyo, Japan

[21] Appl. No.: 179,152

[22] Filed: Aug. 18, 1980

[30] Foreign Application Priority Data

Aug. 20, 1979 [JP] Japan .................. 54-105081

[51] Int. Cl.$^3$ ...................... G01N 27/00; G01N 27/26
[52] U.S. Cl. ..................... 204/1 T; 324/51; 324/71 R
[58] Field of Search .............. 204/1 T, 1 C, 195 R, 204/195 C; 324/444, 449, 51, 71 R, 65 CR

[56] References Cited

U.S. PATENT DOCUMENTS 3,479,256 11/1969 Smith et al. .................. 204/1 T
4,104,579 8/1978 McIvor ..................... 324/65 CR X Primary Examiner—G. L. Kaplan
Attorney, Agent, or Firm—Sherman & Shalloway

[57] ABSTRACT

Disclosed is a method for assaying an iron-exposed portion of a coated steel plate or a processed product thereof, which comprises bringing a surface, to be measured, of the coated steel plate or processed product thereof, a reference electrode and a counter electrode into contact with a buffer solution having a pH value of from 9.0 to 11.0, effecting in this state electrolysis between the counter electrode and the coated steel plate or processed product thereof under such conditions that the voltage of the coated steel plate or processed product thereof to the reference electrode is 0.8 to 1.5 volts as calculated as a saturated calomel electrode, and evaluating the iron-exposed portion by measuring an electric current flowing between the counter electrode and the coated steel plate or processed product thereof or by observing precipitation and deposition of an oxide or hydrated oxide of iron. According to this method, an iron-exposed portion of a coated steel plate or a processed product thereof can selectively be detected and assayed and evaluated precisely without any substantial influence on a metal present as the coating layer very easily by using a simple measurement apparatus. The results obtained according to this method are well in agreement with the results of the actual test made on cans or other processed products of the coated steel plate.

3 Claims, 3 Drawing Figures

METHOD FOR ASSAYING IRON-EXPOSED PORTION OF COATED STEEL PLATE OR PROCESSED PRODUCT THEREOF

BACKGROUND OF THE INVENTION (1) Field of the Invention

The present invention relates to a method for assaying an exposed iron portion of a coated steel plate or a processed product thereof. More particularly, the present invention relates to an assaying method of selectively detecting an exposed iron portion in a coated steel plate such as tinplate (tin-plated steel plate) and effectively determining and evaluating this exposed portion.

(2) Description of the Prior Art

More than 170 years have passed since tinplate was first used as a can-making material. In view of the corrosive actions of the contents, tinplates having a sufficient and necessary amount of plated tin were used for manufacture of cans till quite recently. However, since the price of tin has been increasing and stable supply of tin is not expected, tinplates having a small amount of plated tin are extensively used at the present.

Highly processed cans such as draw-ironed cans have been developed and they have been used for packing contents having a highly corrosive action.

Under such circumstances, a probability of exposure of iron on the can surface is now very high.

Exposure of iron leads to extreme reduction of the life of a can. Accordingly, it is very important that the degree of exposure of iron should be promptly evaluated and occurrence of accidents owing to abnormal dissolution of iron and hydrogen swelling should be prevented.

As the conventional method for assaying and evaluating the metal-exposed portion of a coated can, there is broadly known a so-called Enamel Rater method. Indeed, this method is valuable for measuring all the metal-exposed portions. However, the object of selectively measuring and evaluating the iron-exposed portion among the metal-exposed portions cannot satisfactorily be attained according to this method.

As the conventional method for measuring and evaluating the exposed iron portion in tinplate, there are known an ISV method (Iron Solution Value method) in which a sample is dipped in a solution containing sulfuric acid and hydrogen peroxide as main ingredients and the amount of iron dissolved out is determined and a TCV method in which a sample is dipped in a solution containing acetic acid and hydrogen peroxide as main ingredients and the amount of iron dissolved out is determined. These conventional methods, however, are defective in that since tin also present as the coating layer is simultaneously dissolved out, iron coated with a thin layer of tin is dissolved out and the amount of this iron is included in the amount of exposed iron dissolved out, with the result that the object of precisely evaluating only the exposed iron uncoated portion cannot be attained satisfactorily.

As the method for evaluating a shelf life or the like of an uncoated can, there is known an ATC method in which the tin-iron alloy layer in tinplate is electrochemically assayed. According to this method, the measurement is carried out after the surface tin plating layer has been removed. Therefore, also this method is apparently unsuitable for attaining the above-mentioned object.

As is seen from the foregoing illustration, in each of the known methods for assaying and evaluating an iron-exposed portion in tinplate, tin present as the coating layer is dissolved out or removed. As far as we know, none of the presently available methods is capable of selectively assaying and evaluating an exposed iron portion alone in tinplate without any influence being given to tin present as the coating layer.

SUMMARY OF THE INVENTION

We found that when a coated steel plate such as tinplate or a processed product thereof is subjected to an electrolytic treatment in a specific solution at a specific voltage, an oxidation current of exposed iron can selectively be picked up without any substantial influence on tin or other metal present as the coating layer. The present invention is based on this finding.

It is therefore a primary object of the present invention to provide a method for assaying an exposed iron portion of a coated steel plate such as tinplate or a processed product thereof, in which only the exposed iron portion can selectively be detected and assayed precisely without any substantial influence on tin or other metal present as the coating layer.

Another object of the present invention is to provide a method for assaying an exposed iron portion of a coated steel plate or a processed product thereof, in which the area of the exposed iron portion can be measured and also the position of the exposed iron portion can precisely be detected.

Still another object of the present invention is to provide a method for assaying an exposed iron portion of a coated steel plate or a processed product thereof, in which since the measurement is carried out electrochemically, detection or determination can be carried out without any troublesome operation and can be accomplished in a short time, any particular skill is not required and the measurement can be performed by the use of a very simple apparatus.

More specifically, in accordance with the present invention, there is provided a method for assaying an iron-exposed portion of a coated steel plate or a processed product thereof, which comprises bringing a surface, to be measured, of the coated steel plate or processed product thereof, a reference electrode and a counter electrode into contact with a buffer solution having a pH value of from 9.0 to 11.0, effecting in this state electrolysis between the counter electrode and the coated steel plate or processed product thereof under such conditions that the voltage of the coated steel plate or processed product thereof to the reference electrode is 0.8 to 1.5 volts as calculated as a saturated calomel electrode, and evaluating the exposed iron portion by measuring an electric current flowing between the counter electrode and the coated steel plate or processed product thereof or by observing precipitation and deposition of an oxide or hydrous oxide of iron.

DETAILED DESCRIPTION OF THE PREFERRED EMBODIMENTS

Figure 1:
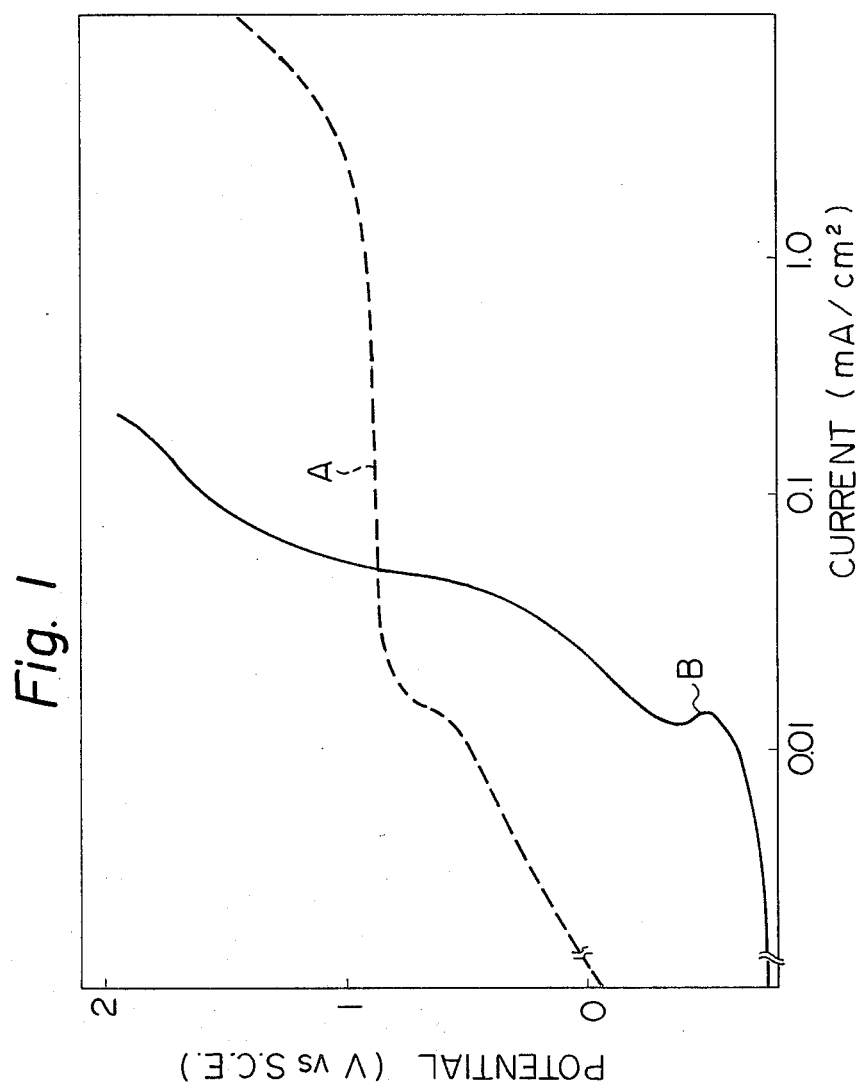
FIG. 1 shows anodic polarization curves of iron and tin as determined in a buffer solution.

The principle of the present invention will now be described with reference to the accompanying drawings. FIG. 1 shows anodic polarization curves of iron (A) and tin (B) as determined in a buffer solution containing 0.2 moles/l of sodium carbonate and 0.2 moles/l of sodium bicarbonate and having a pH value of 10.0. Referring to FIG. 1, when this specific buffer solution is used as an electrolyte and a voltage of a sample to a reference electrode is changed, there is apparently present a voltage region in which an oxidation current of tin can substantially be neglected while an oxidation current of iron (Fe→Fe$^{++}$ +2e) is maintained at a sufficiently high level, that is, a voltage region of 0.8 to 1.5 volts as calculated as the saturated calomel electrode (SCE). The present invention skillfully utilizes the phenomenon shown in FIG. 1. More specifically, according to the present invention, an oxidation current of iron is measured in a voltage region where an oxidation current of tin can substantially be neglected, or precipitation or deposition of an oxide or hydrated oxide of iron formed by this oxidation current of iron is observed, and the exposed iron portion is assayed and evaluated based on the results of such measurement or observation.

Figure 2:
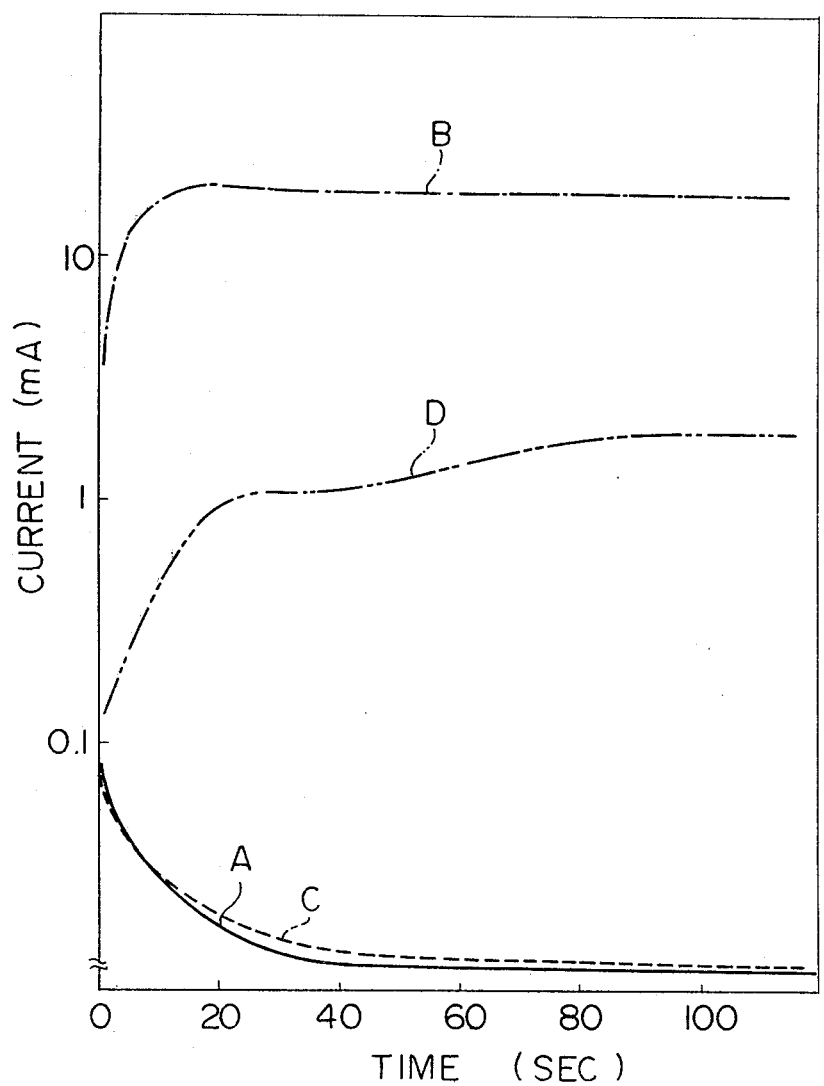
FIG. 2 shows current-time curves as determined with respect to various metal plates.

FIG. 2 shows current-time curves as determined by using the above-mentioned buffer solution with a voltage difference of 1.2 volts as calculated as SCE with respect to a pure tin plate (A, solid line), a steel plate (B, one-dot chain line), a tinplate #100 (C, broken line) and a tinplate having a slightly flawed surface (D, two-dot chain line). From the experimental results shown in FIG. 2, the following can be seen.

(1) In case of a pure tin plate or flawless tinplate, the quantity of the flowing current is about 1/1000 of the quantity of the flowing current in case of a steel plate.
(2) In case of a flawed tinplate, the quantity of the flowing current is about 100 times the quantity of the flowing current in case of a flawless tinplate.
(3) The quantity of the flowing current is proportional to the area of the exposed iron portion.
(4) If iron is exposed to the surface, the time required for the reaction is very short and the measurement results can be obtained in a very short time.

According to the present invention, by using a buffer solution having a pH value within the above-mentioned range and carrying out the electrolysis under the above-mentioned conditions with the use of a counter electrode and a reference electrode, assaying and evaluation can be performed very easily.

As the buffer solution, there is preferably used a buffer solution containing 0.05 to 0.5 moles/l of sodium carbonate and 0.05 to 0.5 moles/l of sodium bicarbonate and having a pH value of 9.0 to 11.0. When this buffer solution is used as the electrolyte, there can be attained various advantages such as mentioned below.

(1) Only ordinary and cheap agents are necessary, and the buffer solution can be prepared very simply and easily.
(2) The life of the buffer solution is long and it can be stored at any place.
(3) The buffer solution is not toxic at all.
(4) When this buffer solution is used, the surface other than the exposed iron portion of the sample is not corroded by the buffer solution.

Various adjuvants may be added to the buffer solution that is used for the electrolytic treatment in the present invention. For example, in a coated steel plate which has been allowed to stand for a long time from the time of preparation, formation of an iron oxide is often observed in the exposed iron portion. In this case, the electrolytic treatment should be conducted for a certain time before the oxidation current is elevated to a certain constant value (see the two-dot chain line in FIG. 2). In this case, in order to shorten the time necessary for the electrolytic treatment, that is, the measurement time, a promoter may be added. A chlorine ion is a preferred promotor. The chlorine ion may be added to the buffer solution in an amount sufficient to eliminate influences of the iron oxide, ordinarily 0.001 to 0.01 moles/l.

Figure 3:
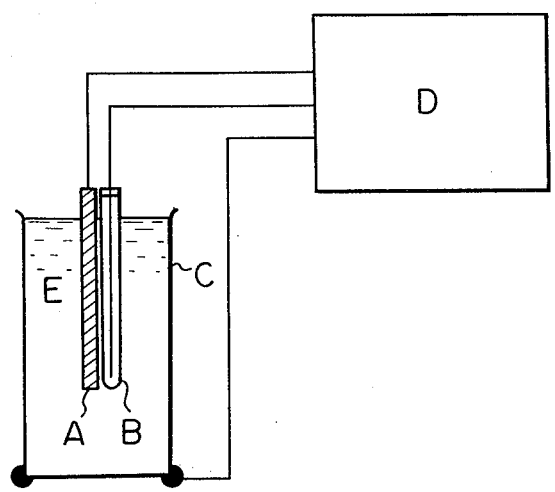
FIG. 3 is a lay-out diagram showing the arrangement of respective members at the time of measurement.

The assaying method of the present invention can be carried out very easily by using a measuring apparatus arranged as shown in FIG. 3. Referring to FIG. 3, symbols A, B, C and D represent a counter electrode, a reference electrode, a can and a constant voltage electrolytic device, respectively. A buffer solution E such as mentioned above is charged in the can C. The counter electrode A and reference electrode B are dipped in the solution E. The electrodes A and B and the sample can C are connected to terminals of the constant voltage electrolytic device, and electrolysis is carried out under conditions controlled so that the voltage of the can C to the reference electrode B is 0.8 to 1.5 volts as calculated as SCE. The current value is displayed on an analog or digital ampere meter, and the current value is recorded if necessary.

Under the above-mentioned measurement conditions, the oxidation current of tin can be neglected, and the oxidation current of iron is proportional to the area of the initial exposed iron portion. Accordingly, the area of the exposed iron portion can be determined and evaluated based on the current value measured.

Known graphite and platinum electrodes may be used as the counter electrode A. A saturated calomel electrode is advantageously used as the reference electrode B, but other reference electrodes such as a saturated silver chloride electrode can also be used. The structure of the constant voltage electrolytic device is well known, and a known electrolytic device can be used in the present invention.

The method of the present invention is applied especially advantageously to determination of dissolution of iron from a processed product of a coated steel plate such as a can. At the measurement of a can, when the buffer solution is filled in the can as shown in FIG. 3, the exposed iron portion can be assayed throughout the inner surface of the can. Ordinarily, a coated steel plate such as tinplate often has latent defects even if it is seemingly flawless. In case of a coated steel plate having a latent defect, if the coated steel plate is subjected to treatments such as bending, flange processing, lap seaming, drawing, ironing, bead processing and curling in the can-forming process, such latent defect is manifested as exposure of iron. According to the assaying method of the present invention, such defect can be detected and evaluated precisely. Of course, a coated steel plate per se and various processed products other than the can may advantageously be tested according to the assaying method of the present invention for determination and evaluation of exposed iron portions. In this case, the buffer solution is charged in an appropriate vessel, a coated steel plate or processed product having cut edges coated is dipped in the buffer solution, and the measurement is carried out in the same manner as described above.

The measurement conditions may be changed freely, so far as the above-mentioned requirements are satisfied. It is one of advantages of the method of the present invention that the temperature dependency is very small. The method of the present invention is ordinarily carried out at room temperature, and a lower or higher temperature may be adopted. Although the time required for the electrolytic treatment varies to some extent according to the surface condition of the coated steel plate which is influenced by the lapse of time from the time of preparation, precise results can ordinarily be obtained stably if the treatment is conducted for at least 5 seconds, especially at least 1 minute.

In the sample which has been subjected to the electrolytic treatment, deposition of an oxide or hydrated oxide of iron is clearly observed in the exposed iron portion. Accordingly, by naked eye observation or microscope observation, the area of the exposed iron portion can be determined and the position of the exposed iron portion can easily be confirmed. This is an additional advantage attained by the present invention.

The present invention has been illustrated with reference to tinplate. By virtue of the advantage that only an oxidation current of iron can be picked up, as will be obvious to those skilled in the art, the method of the present invention can effectively be used for assaying exposed iron portions in coated steel plates other than tinplate, for example, electroplated and melt-plated steel plates, steel plates electrolytically or chemically treated with chromium and/or phosphoric acid, such as TFS (tin-free steel) plates, coated steel plates formed by sputtering, spraying and vacuum evaporation deposition, and enameled and painted steel plates formed by electrodeposition, electrostatic coating, film lamination and the like.

The present invention will now be described with reference to the following Examples that by no means limit the scope of the invention.

EXAMPLE 1

A steel plate and a tin plate, each having a surface area of 1 $cm^2$, was subjected to an electrolytic treatment in 300 ml of an electrolyte shown in Table 1 under conditions shown in Table 1. After the electrolytic treatment had been conducted for 30 seconds, the current value was measured to obtain results shown in Table 1.

Furthermore, two kinds of 200-gram cans having the entire inner face coated with lacquer, which were different in the degree of exposure of iron in the side-seam portion according to the difference of the condition for formation of the side-seam portion, were prepared according to the customary soldering method. These cans were assayed under conditions shown in Table 1 by using the electrolytic apparatus shown in FIG. 3. The measured electrolytic current value and the condition of the inner surface of the can after the treatment are shown in Table 1.

Separately, these two kinds of 200-gram cans A and B were tested according to the conventional enamel rater method. It was found that the obtained values were 28.5 mA in the can A and 15.6 mA in the can B (each being an average value of the values of 10 samples).

From the results shown in Table 1, it will readily be understood that when the electrolytic treatment is carried out under conditions of a pH value of 9 to 11, a test voltage of 0.8 to 1.5 volts to the saturated calomel electrode, sodium carbonate and sodium bicarbonate concentrations of 0.05 to 0.5 mole/l and a chlorine ion concentration lower than 0.01, the oxidation current of iron can be determined effectively with good reproducibility without extreme promotion of the oxidation of iron.

It will also be understood that if the treatment is carried out under the above-mentioned conditions, the degrees of exposure of iron can precisely be discriminated and evaluated in cans differing in the degree of exposure of iron.

TABLE 1

| Run No. | pH Value | $Na_2CO_3$ and $NaHCO_3$ Concentration (mole/l) | $Cl^-$ Concentration (mole/l) | Electrolytic Voltage (V vs SCE) | Counter Electrode | Reference Electrode |
|---|---|---|---|---|---|---|
| 1 | 8.5 | 0.2 | 0.008 | 1.1 | graphite | saturated calomel electrode |
| 2 | 9.5 | 0.2 | 0.003 | 1.1 | " | saturated calomel electrode |
| 3 | 10.5 | 0.2 | 0.003 | 1.1 | " | saturated calomel electrode |
| 4 | 11.5 | 0.2 | 0.003 | 1.1 | " | saturated calomel electrode |
| 5 | 10.0 | 0.8 | 0.003 | 0.7 | " | saturated calomel electrode |
| 6 | 10.0 | 0.8 | 0.003 | 0.9 | " | saturated calomel electrode |
| 7 | 10.0 | 0.8 | 0.003 | 1.8 | " | saturated calomel electrode |
| 8 | 10.0 | 0.8 | 0.003 | 1.5 | " | saturated calomel electrode |
| 9 | 10.0 | 0.8 | 0.003 | 1.7 | " | saturated calomel electrode |
| 10 | 9.8 | 0.08 | 0.003 | 1.2 | " | saturated silver chloride electrode |
| 11 | 9.8 | 0.05 | 0.003 | 1.2 | " | saturated silver chloride electrode |
| 12 | 9.8 | 0.5 | 0.003 | 1.2 | " | saturated silver chloride electrode |
| 13 | 9.8 | 0.7 | 0.003 | 1.2 | " | saturated silver chloride electrode |
| 14 | 10.0 | 0.25 | 0 | 1.2 | platinum wire | saturated calomel electrode |

TABLE 1-continued

| | | | | | | |
|---|---|---|---|---|---|---|
| 15 | 10.0 | 0.25 | 0.001 | 1.2 | " | saturated calomel electrode |
| 16 | 10.0 | 0.25 | 0.015 | 1.2 | " | saturated calomel electrode |

| | 200-Gram Test Can A | | | | 200-Gram Test Can B | |
|---|---|---|---|---|---|---|
| | Electrolytic Current (mA/cm²) | | electrolytic | condition of side-seam | electrolytic | condition of |
| Run No. | steel plate | tin plate | current (mA) | portion | current (mA) | side-seam portion |
| 1 | 41.0 | 0.06 | 2.8 | liner brown deposition | 26.5 | brown deposition on entire surface |
| 2 | 24.0 | 0.05 | 0.15 | brown deposition: one fine point | 1.75 | spot deposition; about 10 points |
| 3 | 24.0 | 0.07 | 0.15 | brown deposition: one fine point | 1.80 | spot deposition; about 10 points |
| 4 | 8.0 | 0.12 | 0.02 | no deposition | 0.31 | no deposition |
| 5 | 2.1 | 0.04 | 0.01 | " | 0.08 | " |
| 6 | 23.0 | 0.04 | 0.15 | brown deposition: one fine point | 1.60 | brown deposition: about 10 points |
| 7 | 25.0 | 0.05 | 0.16 | brown deposition: one fine point | 1.55 | brown deposition: about 10 points |
| 8 | 26.0 | 0.08 | 0.16 | brown deposition: one fine point | 1.75 | brown deposition: about 10 points |
| 9 | 26.0 | 0.50 | 0.34 | no deposition | 4.25 | no deposition |
| 10 | 29.0 | 0.32 | 0.68 | " | 7.20 | " |
| 11 | 23.0 | 0.09 | 0.20 | brown deposition: one fine point | 1.95 | brown deposition: about 10 points |
| 12 | 24.0 | 0.03 | 0.16 | brown deposition: one fine point | 1.65 | brown deposition: about 10 points |
| 13 | 32.0 | 8.2 | 3.2 | linear brown deposition | 30.5 | brown deposition on entire surface |
| 14 | 22.0 | 0.03 | 0.15 | brown deposition: one fine point | 1.45 | brown deposition: about 10 points |
| 15 | 24.0 | 0.03 | 0.16 | brown deposition: one fine point | 1.90 | brown deposition: about 10 points |
| 16 | 28.0 | 0.20 | 2.1 | linear brown deposition | 28.5 | brown deposition on entire surface |

Apple juice, cola and boiled tuna were packed separately into the above-mentioned two kinds of the cans A and B according to customary procedures, and after they had been stored at 37° C. for 6 months, the cans were opened and they were assayed to obtain results shown in Table 2. The number of can tested was 10 in each case.

TABLE 2

| | Actual Pack Test Results | |
|---|---|---|
| | Can A | Can B |
| Apple Juice | | |
| Fe (ppm) | 0.6 | 2.8 |
| H$_2$ (ml) | 0.08 | 0.39 |
| Cola | | |
| Fe (ppm) | 0.25 | 2.8 |
| Number of Perforated Cans | 0 | 2 |
| Boiled Tuna | | |
| H$_2$ (ml) | 0.06 | 0.80 |
| Condition of Inner Face | good | black points on side-seam portion |

From the results shown in Table 2, it will readily be understood that the results of the assay of cans according to the method of the present invention are well in agreement with the results obtained at the actual pack tests made on cans filled with various contents.

EXAMPLE 2

A tinplate #100/25 was printed on the outer face (#25 face) thereof except the portion to be soldered and from this printed tinplate, 250-gram cans (JIS Z-1571) having the uncoated inner face and being different in the degree of exposure of iron were formed. The degree of exposure of iron was controlled according to the bending condition at the time of formation of a side-seam portion or the bumping condition. Then, 202-diameter coated tinplate lids, of which the absence of exposure of iron had been confirmed in advance, were double-seamed to the above cans, and apple juice was hot-packed in the cans and similar coated tinplate lids were double-seamed to the packed cans.

The packed cans were stored at 37° C. for 6 months, and the amount of hydrogen gas accumulated in each can was measured.

The degree of exposure of iron in an empty can was determined according to the method shown in FIG. 3 by using a buffer solution having a Cl$^-$ concentration of 0.03 moles/l, a pH value of 10.0, a sodium carbonate concentration of 0.25 moles/l and a sodium bicarbonate concentration of 0.25 moles/l. The counter electrode used was a graphite rod and the reference electrode used was a saturated calomel electrode. The voltage of the can to the reference electrode was 1.0 volt, and the time for the electrolytic treatment was 30 seconds.

A can prepared in the same manner as described above was electrolyzed with a direct current by using a 2% solution of ammonium thiocyanate according to customary procedures. The can was used as the anode and a stainless steel rod was used as the cathode, and a voltage of 6 volts was applied between the two electrodes. Red reaction inherent of iron thiocyanate was not observed.

The degree of exposure in the empty can, the condition of the inner face after the electrolytic treatment of the present invention and the result of determination of hydrogen gas after 6 months' storage are shown in Table 3. In each case, the number of the tested cans was 10, and each value shown in Table 3 is an average value.

TABLE 3

Results of Assay According to Present Invention

| Run No. | electrolytic current (mA) | condition of inner face of can after electrolytic treatment | Amount (ml) of Hydrogen Gas |
|---|---|---|---|
| 1 | 0.06 | same as before treatment | 0.03 |
| 2 | 0.5 | same as before treatment | 0.09 |
| 3 | 1.8 | deposition (6 points) in side-seam portion | 0.36 |
| 4 | 11.0 | linear deposition in side-seam portion | 2.9 |
| 5 | 23.5 | deposition on entire face of side-seam portion | 7.8 (7 swollen cans among 10 cans) |
| 6 | 38.5 | deposition on entire face of side-seam portion | 16.8 (all cans swollen) |

From the results shown in Table 3, it will readily be understood that the electric current value (average value of 10 samples) determined according to the method of the present invention is well in agreement with the amount of hydrogen accumulated in the can. More specifically, when the electrolytic current value is small, that is, the amount of the iron oxide is small, the amount of hydrogen gas accumulated in the can is small. On the other hand, when the electrolytic current value exceeds 10 mA, the cans were swollen after 6 months' storage.

Incidentally, when the above-mentioned cans were assayed and evaluated according to the above-mentioned conventional enamel rater method, the same results were obtained in all the cans and the degree of corrosion in the respective cans could not be estimated.

EXAMPLE 3

A tinplate #50/25 was coated on the #50 face except an enamel-free portion for soldering with a phenol-epoxy type enamel, and #25 face was printed except a portion for soldering. Cans differing in the degree of exposure of iron were prepared from this tinplate in the same manner as described in Example 1. An easy open end lid of aluminum was double-seamed to one end of the can body, cola was cold-packed and a 202-diameter coated tinplate lid was double-seamed to the other end of the can body. The packed can was stored at 37° C. for 6 months, and the amount of dissolved iron was measured.

The degree of exposure of iron in an empty can was determined in the same manner as described in Example 1 except that the pH value was 9.95, each of the sodium carbonate and sodium bicarbonate concentrations was 0.15 moles/l, the Cl⁻ concentration was 0.07 moles/l and the electrolytic voltage was 1.3 volts.

Similar cans were tested according to the conventional Enamel Rater method (indicated as "ERV") using a 1% aqueous solution of sodium chloride.

The obtained results are shown in Table 4.

Cans in which the electrolytic current value determined according to the method of the present invention were small were characterized by a small amount of dissolved iron and they had good storage characteristics. On the other hand, in cans where the electrolytic current value was large and deposition was conspicuous, the amount of dissolved iron was large and perforation was observed. From Table 4, it will readily be understood that the evaluation values (ERV) according to the conventional Enamel Rater method were not in agreement with the results obtained at the actual pack test.

TABLE 4

| | Results of Assay According to Method of Present Invention | | Results (ERV, mA) of Evaluation According to Conventional Method | Amount (ppm) of Dissolved Iron |
|---|---|---|---|---|
| Run No. | electrolytic current (mA) | condition of inner face of can after electrolytic treatment | | |
| 1 | 0.08 | same as before treatment | 180 | <0.1 |
| 2 | 0.20 | same as before treatment | 230 | 0.4 |
| 3 | 4.8 | deposition at many points in side-seam portion | 92 | 4.1 |
| 4 | 13.0 | linear depositon in side-seam portion | 110 | 12 (2 perforated cans among 10 cans) |
| 5 | 24.5 | deposition on entire face of side-seam porton | 130 | 38 (6 perforated cans among 10 cans) |

EXAMPLE 4

Empty cans prepared in the same manner as described in Example 2 were stored at 37° C. for 6 months, and they were subjected to the electrolytic treatment by using an electrolyte having a pH value of 10.0, a sodium carbonate concentration of 0.1 mole/l, a sodium bicarbonate concentration of 0.1 mole/l and a chlorine ion concentration of 0.003 moles/l while the voltage of the can to the saturated calomel electrode was adjusted to 1.1 volts. Results of the assay conducted just after preparation of the cans and after 6 months' storage are shown in Table 5.

TABLE 5

| | Electrolytic Current Value (mA) | |
|---|---|---|
| | Cl⁻ concentration of 0 mole/l | Cl⁻ concentration of 0.003 moles/l |
| just after preparation | 1.32 | 1.33 |
| after storage at 37° C. for 6 months | 1.01 | 1.32 |

From the results shown in Table 5, it will readily be understood that in case of cans just after preparation, the electrolytic current value obtained by using an electrolyte free of chlorine ions is substantially the same as the value obtained by using a chlorine ion-containing electrolyte but in case of cans which have been allowed to stand for a long time, a very high effect can be obtained by incorporation of chlorine ions.

EXAMPLE 5

From 2 kinds of tinplates #100, 2T bending test pieces were prepared, and the test pieces were sealed with a wax except a bent portion having a length of 4 cm. The test pieces were subjected to electrolytic treatment in a beaker having a capacity of 200 ml by using a platinum wire as the counter electrode and a saturated silver chloride electrode as the reference electrode. The electrolyte used had a pH value of 9.5, a sodium carbonate concentration of 0.15 moles/l, a sodium bicarbonate concentration of 0.15 moles/l and a chlorine ion concentration of 0.005 moles/l. The voltage of the test piece to a saturated silver chloride as the reference electrode was 1.3 volts, and the time for the electrolytic treatment was 30 seconds. Separately, uncoated cans were prepared from the above-mentioned tinplates. Apple juice was packed in these cans, and the packed cans were stored at 37° C. for 6 months. The amounts of dissolved iron and accumulated hydrogen gas were measured. The obtained results are shown in Table 6.

For comparison, the above tinplates were tested according to the conventional iron solution value method (ISV method). The obtained results are shown in Table 6.

TABLE 6

| Electrolytic Current (mA) at Electrolysis of Bending Test Piece | ISV ($\mu$g/3 in$^2$) of Tinplate | Results of Actual Pack Test | |
|---|---|---|---|
| | | Fe (ppm) | H$_2$ (ml) |
| 0.3 | 12 | 0.80 | 0.07 |
| 11.5 | 10 | 48.9 | 6.8 |

It is ordinarily accepted that a tinplate having an iron solution value (ISV) smaller than 20 $\mu$g/3 in$^2$ is highly corrosion-resistant. However, practical properties are remarkably different among these tinplates. Accordingly, the ISV method is not valuable when the contents are highly corrosive. In contrast, as is seen from Table 6, the results of the assay according to the method of the present invention are well in agreement with the results obtained at the actual pack test.

EXAMPLE 6

Tinplates having a plate thickness of 0.30 mm and a tin plating thickness of #25, #50, or #75 were formed into drawn-ironed can bodies having a diameter of 52.5 mm and a height of 133.1 mm for packing of carbonated drinks. These can bodies were degreased, washed and dried, and they were subjected to electrolytic treatment by using a saturated silver chloride electrode as the reference electrode and a platinum wire as the counter electrode to determine the degree of exposure or iron. The electrolyte used had a pH value of 10.0, a sodium carbonate concentration of 0.2 moles/l, a sodium bicarbonate concentration of 0.2 moles/l and a hydrochloric acid concentration of 0.003 moles/l. Can bodies prepared from the tinplate having a tin plating thickness of #25 were degreased, washed, chemically treated with phosphoric acid by the spraying method and dried, and then, they were subjected to the electrolytic treatment in the same manner as described above.

Separately, can bodies formed under the same conditions as described above were subjected to outer surface printing and inner face coating, and lemon-lime carbonated drink or cola was packed in these cans. According to customary procedures, aluminum lids were double-seamed. Then, the packed cans were stored at 37° C. for 1 year, and assay of dissolved iron and evaluation of the condition of the inner face were carried out. Furthermore, in case of coated cans, ERV was determined in the same manner as described in Example 3.

The obtained results are shown in Table 7.

From the results shown in Table 7, it will readily be understood that the assaying method of the present invention can effectively be utilized to evaluation of drawn-ironed can bodies.

TABLE 7

| | Can | | Assay Results According to Present Invention | | ERV (mA) According to Conventional Method | Results of Actual Pack Tests | | | |
|---|---|---|---|---|---|---|---|---|---|
| | | | | | | cola | | lemon-lime | |
| Run No. | tinplate | surface treatment | electrolytic current (mA) | inner face condition | | amount (ppm) of dissolved iron | number of pinhole cans | amount (ppm) of dissolved iron | condition of inner face |
| 1 | #75 | not applied | 30–50 | not changed | 0 | <0.2 | 0/100 | <0.2 | not changed |
| 2 | #50 | not applied | 100–120 | 2 to 5 fine spots | 0 | 0.1–0.4 | 0/100 | 0.1–0.8 | 2 to 3 fine corrosion spots |
| 3 | #25 | not applied | 500–700 | extreme deposition | 0 | 0.5–1.5 | 3/100 (swollen cans) | 0.5–3.5 | many corrosion spots |
| 4 | #25 | applied | 150–200 | 5 to 10 fine spots | 0 | 0.1–0.3 | 0/100 | 0.2–1.5 | 2 to 5 fine corrosion spots |

What we claim is:

1. A method for assaying an exposed iron portion of a tin-plated steel plate or a processed product thereof, which comprises bringing a surface, to be measured, of the tin-plated steel plate or processed product thereof, a reference electrode and a counter electrode into contact with a buffer solution having a pH value of from 9.0 to 11.0, effecting in this state electrolysis between the counter electrode and the tin-plated steel plate or processed product thereof as anode under such conditions that the voltage of the tin-plated steel plate or processed product thereof to the reference electrode is 0.8 to 1.5 volts calculated as a saturated calomel electrode, and evaluating the exposed iron portion by measuring an electric current flowing between the counter electrode and the tin-plated steel plate or processed product thereof or by observing precipitation and deposition of an oxide or hydrated oxide of iron.

2. An assaying method according to claim 1, wherein the buffer solution is an aqueous solution containing 0.05 to 0.5 moles/l of sodium carbonate, 0.05 to 0.5 moles/l of sodium bicarbonate and 0.001 to 0.01 mole/l of a chlorine ion.

3. An assaying method according to claim 1, wherein the processed product of the coated steel plate is a can of a tinplate.

* * * * *